United States Patent
Kudo et al.

(10) Patent No.: US 7,767,442 B2
(45) Date of Patent: Aug. 3, 2010

(54) BIOCHEMICAL SENSOR AND MEASURING DEVICE HAVING CHANNEL STRUCTURE FOR SAMPLE COLLECTION

(75) Inventors: Jun Kudo, Nara (JP); Tomohisa Kawata, Nara (JP); Mikihiro Yamanaka, Soraku-gun (JP)

(73) Assignee: Sharp Kabushiki Kaisha, Osaka (JP)

( * ) Notice: Subject to any disclaimer, the term of this patent is extended or adjusted under 35 U.S.C. 154(b) by 615 days.

(21) Appl. No.: 11/607,010

(22) Filed: Dec. 1, 2006

(65) Prior Publication Data

US 2007/0134748 A1 Jun. 14, 2007

(30) Foreign Application Priority Data

Dec. 9, 2005 (JP) .............................. 2005-356385

(51) Int. Cl.
- *C12M 1/34* (2006.01)
- *C12M 3/00* (2006.01)
- *G01N 21/00* (2006.01)
- *G01N 31/22* (2006.01)

(52) U.S. Cl. .............. 435/287.8; 435/287.9; 435/288.4; 435/288.5; 422/57; 422/58

(58) Field of Classification Search ........................ None
See application file for complete search history.

(56) References Cited

U.S. PATENT DOCUMENTS 6,716,629 B2 * 4/2004 Hess et al. .................. 435/420
2004/0171017 A1 * 9/2004 Firrao ............................ 435/6

FOREIGN PATENT DOCUMENTS

JP 2004-083501 A 3/2004

OTHER PUBLICATIONS

Zhou et al., Immunoassays for cortisol using antibody-doped sol-gel silica, J. Mater. Chem., 14, pp. 2311-2316 (2004).
Mukai, et al., "Formation of monolithic silica gel microhoneycombs (SMHs) using pseudosteady state growth of microstructural ice crystals", Chem. Commun., pp. 874-875 (2004).

* cited by examiner

*Primary Examiner*—Unsu Jung
*Assistant Examiner*—Leon Y. Lum
(74) *Attorney, Agent, or Firm*—Nixon & Vanderhye, P.C.

(57) ABSTRACT

A biochemical sensor capable of detecting a prescribed target substance in a specimen in a short time period with high sensitivity and measuring the amount thereof has a surface and a rear surface, and channels formed from the surface to the rear surface, allowing influx of the specimen. An inner circumferential surface of the channels is formed of porous material. The porous material carries, in its pores, functional substance having a function of forming a reactant by the interaction with the target substance.

16 Claims, 5 Drawing Sheets

BIOCHEMICAL SENSOR AND MEASURING DEVICE HAVING CHANNEL STRUCTURE FOR SAMPLE COLLECTION

CROSS-REFERENCE TO RELATED APPLICATION

This non-provisional application claims priority under 35 U.S.C. §119(a) on Japanese Patent Application No. 2005-356385 filed on Dec. 9, 2005, the entire contents of which are hereby incorporated by reference.

BACKGROUND OF THE INVENTION

1. Field of the Invention

The technology disclosed herein relates to a sensor for detecting chemical substances or biological molecules in a specimen and, more specifically, to a biochemical sensor and a measuring device capable of detecting chemical substances or biological molecules in a specimen quickly in a simple manner.

2. Description of the Background Art

Recently, increase in lifestyle-related diseases has come to be a major problem. Health problems caused by environmental destruction are also increasing. Further, increasingly complex living conditions leads to larger population suffering from repression and psychic stress. In such a modern society, physical and mental health is naturally a matter of serious concern.

To maintain physical and mental health and to enjoy improved quality of life, symptomatic treatment, that is, treatment taken after one became aware of distinct abnormality, would be insufficient. To stay fit, prevention, such as taking a regular medical check-up, is desirable for early detection and early treatment of potential physical and mental abnormality.

Medical check-up involves collection, analysis and diagnosis of specimens. Conventionally, appropriate facility and well-trained personnel were considered indispensable to appropriately conduct these operations. As a result, it was a common practice to have a medical check-up at a hospital. Technical development, however, has enabled medical check-up in a manner different from the conventional method. Specifically, advancement in biotechnology and improvement in communication technology such as the Internet contribute to such new approach.

For instance, the following approach is now available. Specifically, the subject collects and analyzes a specimen at his/her home using a device that can be operated with little practice, and obtains data of the specimen. The subject transmits the data to a hospital through the Internet, and a doctor makes a diagnosis based on the transmitted data. The result of diagnosis is again sent to the subject at home through the Internet. Such medical check-up does not require a visit to the hospital, and hence, it is not time-consuming. Therefore, such an approach is convenient and effective to maintain one's physical and mental health.

In order to spread such method of medical check-up, however, it is necessary to establish technique necessary therefor. To enable medical check up as part of daily life, it is essential that the specimen can be collected and analyzed quickly in a simple manner. Therefore, a device for collecting the specimen for medical check up must be small and allow easy operation. Further, analysis of the specimen must also be done without requiring large-scale equipment.

At present, biochemical sensing techniques are promising to meet such demands. An example is a lavatory pan allowing checking of one's health condition based on excrements. Specific examples of other biochemical devices will be described in the following, considering physical aspects and mental aspects separately.

As regards the physical aspect, it is noted that the number of patients afflicted with lifestyle-related diseases has been increasing, due to poor diet and un-orderly lifestyle. A representative example is diabetes. For early detection and treatment of diabetes, and for improving quality of life of diabetic patients, it is essential to ascertain condition of the disease on a daily basis. To meet such a demand, a disposable glucose sensor that quickly detects blood glucose level useful for determining diabetic condition has been practically used. The glucose sensor is an example of the biochemical device.

As regards the mental aspect, more and more people are stressed-out in an increasingly complex society. Heavy stress may lead to grave consequences. To relieve stress as early as possible, first of all, it is necessary to know that one is under stress. For this purpose, a device that can accurately measure the stressed state of a user is desired. A specific method of detecting stress includes collection of blood, urine or saliva and detection of cortisol (one of vital hormones) as stress-related substance contained therein. A biochemical device is also used for detecting cortisol.

As described above, currently, there is a need for a technique that enables quick and simple diagnosis of both physical and mental health condition, and development of more advanced technique is desired. Therefore, development of biochemical technique that can detect information related to physical and mental health condition with high sensitivity, at high speed, in a simple manner and at a low cost is an important task. Such technique would be effective not only for medical check up but also for other applications.

As a technique realizing biochemical sensing with high sensitivity, use of antigen-antibody reaction and porous materials has been known. In one such technique, for the antigen as the target material to be detected (hereinafter simply referred to as the "target"), the antibody is carried adsorbed in the pores of the porous material. Application of such a technique is not limited to the antigen-antibody reaction, and it is generally applicable to two substances that react uniquely to each other. In the following description, however, examples will be described in which the antigen is the target and the antibody is the substance that is adsorbed and carried in the pores.

Porous silica is known as a material that realizes a structure for adsorbing and carrying the antibody and does not deactivate the antibody. Japanese Patent Laying-Open No. 2004-83501 discloses a bio-sensing technique using porous silica. Porous silica is formed by sol-gel method using organo-silicate as a main raw material or by freeze drying using inorgano-silicate. The former will be referred to as sol-gel porous silica, and the latter will be referred to as freeze-dried porous silica.

Such porous silica adsorbs the antibody in the minute pores of the porous material without damaging its function. Further, the porous silica is translucent. A biochemical sensor may be fabricated using the porous silica having such characteristics. In the following, a method of detecting an antigen using the biochemical sensor will be described.

First, a prescribed amount of antigen, fluorescence-labeled with fluorescent dye molecules and the like, is prepared as a standard sample. Next, sample specimen containing antigen as the target, which is not fluorescence-labeled, and the standard sample containing the antigen fluorescence-labeled with fluorescent dye molecules as described above are mixed. The mixed sample is applied to the porous silica having the antibody adsorbed and carried therein, to cause a reaction between the antigen in the mixed sample and the antibody adsorbed in the porous silica. By the antigen-antibody reaction, the antigen contained in the sample and the antibody adsorbed in porous silica are bonded. When the bonded antigen and antibody are irradiated with excitation light that excites the fluorescent dye molecules used for the fluorescence labeling, the antigen derived from the standard sample emits fluorescent light. By detecting intensity of the emitted fluorescent light using a photodetector, the amount of antigen contained in the sample specimen can be measured in the following manner.

The antigen in the mixed sample can be divided to two classes: those derived from the standard sample (fluorescence-labeled) and those derived from the sample specimen (not fluorescence-labeled). The amount of antigen derived from the standard sample is invariable. On the contrary, the amount of antigen derived from the sample specimen varies dependent on the amount of antigen in the sample specimen. Therefore, abundance ratio of the antigen derived from the standard sample and the antigen from the sample specimen varies. The amount of antibody in the porous silica is invariable. Accordingly, the abundance ratio of antigen from the standard sample and the antigen from the sample specimen of the whole antigen bonded to the antibody varies in accordance with the abundance ratio of antigen from the standard sample and the antigen from the sample specimen in the mixed sample. The fluorescent light is emitted only by the antigen derived from the standard sample, and therefore, the fluorescence intensity varies in accordance with the abundance ratio. As a result, the amount of antigen in the original sample specimen can be known from the fluorescence intensity, in the following manner.

A plurality of mixed samples having various different compositions of antigen fluorescence-labeled with fluorescent dye molecules and antigen not labeled are prepared beforehand. Fluorescent light detection is done in the manner as described above for each of these mixed samples. Based on the thus obtained fluorescence intensities, a calibration curve is formed. The calibration curve indicates, as a graph, expected fluorescence intensity based on the mixture ratio of the labeled antigen and unlabeled antigen. When there is an unknown amount of antigen fluorescence-labeled with fluorescent dye molecules, it is possible to know the amount of antigen, by mixing the antigen with a known amount of standard sample, measuring variation in the fluorescence intensity, and comparing the intensity with the calibration curve.

The prior art disclosed in Japanese Patent Laying-Open No. 2004-83501 mentioned above relates to a technique of fixing antibody in minute pores in the sol-gel porous silica having minute pores formed in the form of a film. By this technique, the antibody can stably be fixed.

Even in this method, however, the amount of antibody that can effectively be carried in the minute pores and utilized for measurement is limited by the area of the minute pores formed as a film on a surface of a base material. This limitation leads to insufficient accuracy of antigen detection.

Further, generally it takes time for the antigen to penetrate and reach the antibody adsorbed and carried in the minute pores and to be bonded to the antibody. As the rate of detection is controlled by the rate of penetration, it is difficult to realize highly sensitive and quick sensing by the technique described in Japanese Patent Laying-Open No. 2004-83501.

J. C. Zhou, et al., *Immunoassays for cortisol using antibody-doped sol-gel silica*, J. Mater. Chem., 2004, 14, 2311-2316 discloses a solution to the problems of insufficient detection sensitivity and difficulty in highly sensitive and quick sensing. The technique disclosed by Zhou et al. is directed to a porous silica structure adsorbing and carrying a substance functionalized to react to a prescribed substance such as the antibody and to generate a reactant.

The object of the invention disclosed by Zhou et al. is to detect cortisol. Zhou et al. further discloses a technique utilizing antibody carried by porous silica gel formed by sol-gel method using organo-silicate raw material.

According to Zhou et al., to fabricate the porous structure, first, tetramethylorthosilicate, water and diluted hydrochloric acid are mixed, to prepare silica hydrosol. The mixture is further mixed with phosphate buffer containing anti-cortisol antibody. By sol-gel method of gelating the mixture, a porous silica monolith body containing the anti-cortisol antibody is formed.

By the technique disclosed by Zhou et al., a porous silica monolith body is formed that adsorbs and carries anti-cortisol antibody in the minute pores. Therefore, as compared with the disclosure of Japanese Patent Laying-Open No. 2004-83501 in which the antibody is adsorbed and carried by the porous material formed as a film on a surface of a base material, sensitivity of antigen detection can be improved. The disclosure of Zhou et al., however, still has a limitation in the amount of antibody that can be used for measurement, and hence, detection sensitivity is insufficient. The reason will be described in the following.

When antigen molecules are applied to the monolith body, the antigen molecules may react rather quickly to the antibody molecules adsorbed and carried near the surface of the monolith body. For the antigen to reach and react to the antibody adsorbed and carried at positions deep inside from the surface, it is necessary that the antigen molecules pass through the porous mesh structure and to diffuse deep inside the monolith body. It naturally takes a long time for the antigen molecules to reach the deep position in the monolith body and, as a result, the antigen-antibody reaction also takes long time.

In order to solve this problem, it may be possible to fabricate a porous silica monolith body that is relatively thin (having the thickness, for example, of 1 mm). Such a monolith body, however, still has a problem. Specifically, the diffusion length in the monolith body is typically in proportion to the root of diffusion time. When compared with a monolith thin film formed of the same material and having the thickness of 10 µm, passage through the monolith body of 1 mm takes $10^4$ times longer time. Specifically, when a sol-gel silica monolith body of a simple structure is used, the antigen cannot sufficiently penetrate to the antibody existing at a deep position until after a long time, even if the thickness is as thin as 1 mm. Therefore, the amount of antibody available for reaction with the antigen for a short period of time is limited to the antibody adsorbed and carried on and near the surface of the monolith body. In such a biochemical sensor, the amount of antibody that can react to the antigen is substantially in proportion to the surface area of the monolith body. As a result, if the monolith body has small surface area, the amount of antigen-antibody reaction becomes small, and hence, it is difficult to realize a sensor capable of highly sensitive detection. On the other hand, if the surface area is made larger, handling of the monolith body becomes troublesome.

Specifically, in the technique disclosed in Zhou et al., when antigen detection is to be done effectively utilizing antibody carried at positions deep inside the monolith body, the time for measurement becomes undesirably long. When the time for measurement is to be reduced while the monolith body has small surface area, detection intensity would be insufficient. When the surface area of the monolith body is increased, handling becomes troublesome.

Conditions related to sensor sensitivity will be described with reference to specific examples. As an example of detection of very small amount of target, consider detection of stress-related substance. An example of such substance is cortisol in saliva. In order to obtain significant data of cortisol (MW:362) in saliva, typically, measurement of concentration in the range of about 1.0 to about 30.0 pmol/ml is necessary. The technique disclosed in Zhou et al. allows detection of cortisol in saliva only in the range of 27.6 pmol to 2.76 nmol/ml. From the viewpoint of obtaining significant data, necessary measurable ranges of other substances are as follows. As to human salivary chromogranin A (human CgA) (MW:68000), detection of a small amount of about 0.4 to 1.2 pmol/ml is necessary. As to immuno globulin (MW:200000), detection of a small amount of about 0.5 to 5.0 nmol/ml is necessary.

The technique disclosed in Zhou et al. is advantageous in that, compared with the amount of antibody adsorbed and carried on the porous body formed only at and near the surface of the base material, larger amount of antibody can be adsorbed. It is still impossible, however, to detect the necessary amount of substance with sufficient sensitivity in a short period of time, and to attain higher sensitivity, detection requires long time.

SUMMARY OF THE INVENTION

Therefore, technology disclosed herein provides, e.g., a biochemical sensor capable of detecting a desired substance with high sensitivity in a short period of time and measuring the amount thereof.

The technology disclosed herein also provides a biochemical sensor capable of detecting an antigen with high sensitivity in a short period of time and measuring the amount thereof.

The technology disclosed herein further provides a biochemical sensor capable of detecting a plurality of substances with high sensitivity in a short period of time and measuring the amount thereof.

According to a first aspect, the technology disclosed herein provides a biochemical sensor for detecting a prescribed target substance contained in a specimen of liquid phase or gas phase, including a sensor structure having a surface and a channel formed penetrating from a first region to a second region of the surface, allowing influx of the specimen. An inner circumferential surface of the channel is formed of a porous material. The biochemical sensor further includes a functional substance carried in the porous material forming the inner circumferential surface of the channel, having a function of forming reactant by an interaction with the prescribed target substance.

In the biochemical sensor, the specimen in liquid phase or gas phase readily flows into the sensor structure through the channel. As the inner circumference of the channel is formed of porous material, the specimen quickly infiltrates into the porous material. Thus, the functional substance carried on the wall of the porous material reacts to the prescribed target material contained in the specimen infiltrated through the minute pores in a short period of time. Such a process is readily realized by immersing the sensor structure in the specimen or by putting the sensor structure in the flow of the specimen. As a result, the target substance in the specimen can be detected quickly with high sensitivity by a relatively easy manner, using only a small amount of specimen.

Preferably, the prescribed target substance includes a prescribed antigen; and the functional substance includes an antibody causing an antigen-antibody reaction with the prescribed antigen.

In the biochemical sensor, the prescribed antibody is carried by the porous material forming the inner circumference of the channel. The antigen in the specimen reaches the antibody in a short time, through the channel and the pores at the inner circumference of the channel. Therefore, antigen-antibody reaction takes place in a short period of time with the prescribed antigen contained in the specimen. As a result, the prescribed antigen in the specimen can be detected quickly with high sensitivity by a relatively easy manner.

Preferably, the prescribed functional substance is an enzyme, and the prescribed target substance generates a known reactant by a prescribed reaction caused in the presence of the enzyme.

In the biochemical sensor, the prescribed enzyme is carried by the porous material forming the inner circumference of the channel. The target substance in the specimen reaches the portion where the enzyme exists, in a short time through the channel and the pores at the inner circumference of the channel. Therefore, the target substance contained in the specimen causes a prescribed reaction to the prescribed enzyme. By measuring the amount of reactant, the prescribed target substance in the specimen can be detected quickly with high sensitivity in a relatively easy manner.

Preferably, the biochemical sensor is formed of a prescribed translucent porous material, and the inner circumferential surface of the channel is formed of the porous material of the sensor structure.

The biochemical sensor allows easy measurement of light emitted from the reactant when the reactant resulting from a prescribed reaction is irradiated with light from a light source. Therefore, when a known amount of standard target substance labeled with fluorescent dye substance is mixed in the specimen, the amount of target substance in the specimen that reacted to the functional substance can be measured by a simple method of measuring fluorescence intensity. As a result, the amount of prescribed target substance in the specimen can be detected quickly with high sensitivity in a relatively easy manner.

Preferably, the sensor structure has a plurality of the channel structures formed therein. The sensor structure has a cylindrical shape having a first end surface, a second end surface parallel to the first end surface, and a side surface connecting outer circumferences of the first end surface and the second end surface. Each of the plurality of channels is formed to connect the first end surface to the second end surface.

As the channel is formed to connect the first end surface and the second end surface, the specimen flowing to the sensor structure from, for example, one end surface, smoothly flows through the channel to the other end surface. The flow of specimen is not hindered by the sensor structure, and a large amount of specimen can be processed by the sensor. When a plurality of channels are formed, and further, when the channels are formed with central axes of channels made parallel to each other, such effect can further be enhanced.

When the sensor is formed to have a cylindrical shape with the first and second end surfaces parallel to each other, handling of the sensor becomes easy. Particularly, when the first end surface is made perpendicular to the side surface, it becomes possible to stack the sensors.

When the cross-sectional shape of the channel is made polygonal, for example, a regular hexagon, the sensor structure can readily be formed by utilizing self-organization of substance in the natural world.

According to a second aspect, the technology disclosed herein provides a biochemical sensor including a first layer sensor implemented with any of the above-described biochemical sensors, and a second layer sensor implemented with any of the above-described biochemical sensors arranged on a first surface of the first layer sensor. The target substance for the first layer sensor and the second layer sensor may be the same or different.

In the biochemical sensor, by the sensor having two-layered structure, a prescribed substance contained in the specimen can be detected. When the two sensors are adapted to detect one same substance, sensitivity of detection can be improved and the detection can be done in a shorter time. When the two sensors are adapted to detect different substances, it becomes possible to detect two substances by one operation. As a result, a biochemical sensor capable of detecting the prescribed substance in the specimen quickly with high sensitivity can be provided.

According to a third aspect, the technology disclosed herein provides a measurement unit, including: a light emitting device for emitting light of a prescribed wavelength; an optical element turning the light from the light emitting device to parallel light beams; and a light intensity detecting device arranged to receive light from the biochemical sensor having a sensor structure formed of a prescribed, translucent porous material arranged in the parallel light beams turned by the optical element, for detecting intensity of light having a prescribed wavelength, of the light from the biochemical sensor.

By the reaction between the target substance contained in the specimen and the functional substance carried on the wall, reactant is generated in the biochemical sensor. The sensor structure of the biochemical sensor containing the reactant is irradiated with light. The sensor is translucent, and therefore, the light proceeds through the sensor structure and if there is any reactant along the way, irradiates the reactant. When a mixture of a known amount of standard target substance labeled with fluorescence-labeling substance and an unknown amount of target substance as the object of measurement is used as a sample, only the reactant derived from the standard target substance emits fluorescent light, and the reactant derived from the target substance as the object of measurement does not emit fluorescent light. Further, the sum of reactants from the two substances is defined by the amount of functional substance in the sensor, and the ratio is determined by the ratio of the amount of standard target substance and the target substance as the object of measurement in the mixed sample. Therefore, fluorescence intensity is in correspondence to the mixture ratio of the reactant derived from the standard target substance and the reactant derived from the target substance as the object of measurement. By measuring the fluorescence intensity and comparing the intensity with a calibration curve prepared beforehand, the amount (concentration) of the target substance as the object of measurement can be known. Specifically, by the simple means of optical measurement using fluorescent dye molecules and the like, the amount of target substance in the specimen can be measured.

For the measurement, the biochemical sensor, which is transparent, in accordance with the first aspect of the technology disclosed herein may be used, and therefore, the reaction is quick and highly sensitive. As a result, a biochemical sensor capable of detecting a prescribed substance in a specimen quickly with high sensitivity in a relatively easy manner can be provided.

As described above, the biochemical sensor in accordance with an example embodiment comprises walls separating a plurality of micro-channels. The walls form a hexagon or the like, to provide a honeycomb structure (hereinafter it is referred to as a honeycomb structure), and the walls are functionalized. Here, "functionalized" means a substance having a function of generating a reactant through a reaction with a prescribed target substance (in the specification, the substance having such a function will be referred to as "functional substance") is adsorbed and carried on a surface and inside of a material.

Therefore, chemical substances and biological molecules in the specimen can quickly be detected with high sensitivity. As a result, chemical substances and biological molecules in the specimen can quickly be detected with high sensitivity by a relatively simple method, using only a small amount of specimen.

Further, the biochemical sensor in accordance with an example embodiment allows stacking of a plurality of honeycomb structures each being functionalized. Therefore, it is possible to detect a plurality of chemical substances and biological molecules in the specimen in parallel. As a result, efficient detection of a plurality of substances becomes possible.

The foregoing and other objects, features, aspects and advantages of the present invention will become more apparent from the following detailed description of the present invention when taken in conjunction with the accompanying drawings.

DETAILED DESCRIPTION

Structure

Figure 1:
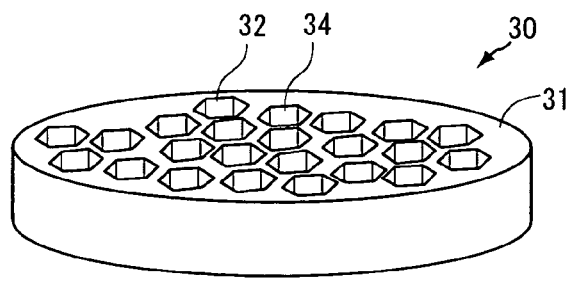
FIG. 1 is a schematic perspective view of a honeycomb structure 30 as a whole in accordance with an example embodiment.
Figure 2:
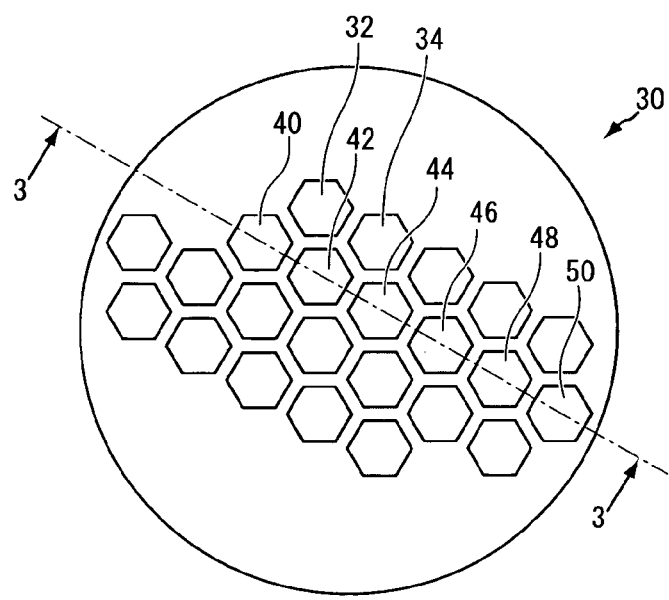
FIG. 2 is a plan view of an example honeycomb structure.
Figure 3:
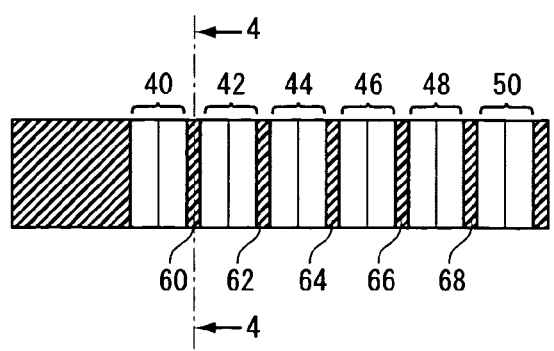
FIG. 3 is a cross-sectional view of honeycomb structure taken along one-dotted line 3-3 of FIG. 2.

Referring to FIGS. 1 to 3, a honeycomb structure 30 has a disk-shape of a prescribed thickness, formed of a porous material such as freeze-dried silica. Honeycomb structure 30 has a flat cylindrical shape, with an upper surface 31 and a lower surface (not shown) parallel to each other. The side surface of the cylinder perpendicularly crosses the upper surface 31 and the lower surface.

Honeycomb structure 30 has a plurality of micro-channels 32, 34, 40, 42, 44, 46, 48 and 50 (hereinafter simply referred to as "micro-channels 32" or "micro-channels 40") passing through the upper surface 31 and the lower surface, formed with a prescribed line being a central axis. In the present embodiment, cross-sectional shape of each micro-channel in a plane parallel to the upper surface 31 is hexagonal.

Referring to FIGS. 2 and 3, honeycomb structure 30 includes walls 60, 62, 64, 66, and 68 (hereinafter simply referred to as "walls 60") separating the plurality of micro-channels from each other. Walls 60 are formed of porous material and define inner circumference of micro-channels 32 and the like, with the surface and inside being functionalized. Here, "functionalized" means that a substance (such as antibody with respect to the antigen) having the function of binding to a target such as the chemical substance or biomolecules (such as the antigen) by some interaction exists on the surface of the porous material and on the inner surface of minute pores. The target can be detected, utilizing the substance existing on the surface and inside of the functionalized walls 60 and the like.

Figure 4:
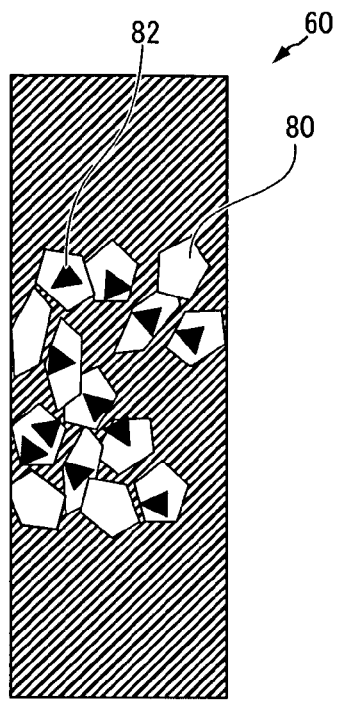
FIG. 4 is a schematic cross-sectional view of the wall in of the honeycomb structure of FIG. 1.

FIG. 4 is a schematic enlarged cross-section of the wall viewed from the direction of one-dotted line 4-4 of FIG. 3. Referring to FIG. 4, wall 60 has numerous minute pores 80, and antibody molecules 82 are adsorbed and carried in these minute pores.

<Measurement of Antigen Amount>

Figure 5:
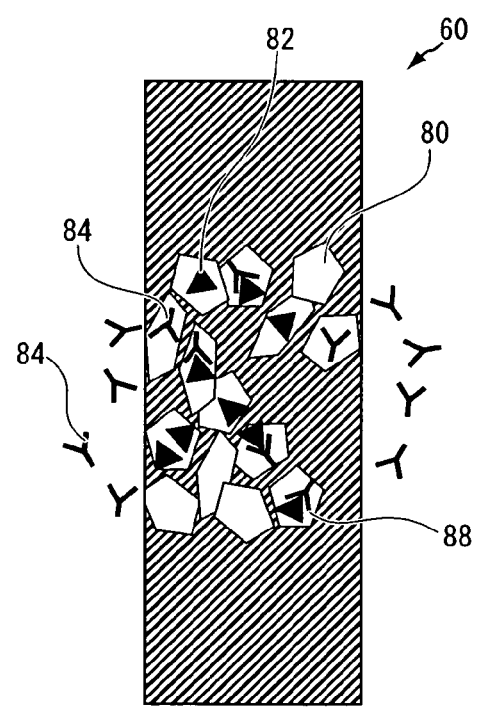
FIG. 5 is a schematic cross-sectional view of the wall in an example honeycomb structure after antigen-antibody reaction.

Referring to FIG. 5, the method of measuring the amount of antigen using the antigen-antibody reaction in honeycomb structure 30 will be described.

Referring to FIG. 5, as already described, walls 60 and the like (see FIG. 3) separating micro-channels 40-50 from each other in honeycomb structure 30 (see FIG. 1) are formed of a porous structure having a large number of minute pores. Specifically, the inner circumference of micro-channels 40-50 is formed of a porous material including a plurality of minute pores. It is noted, however, that as the wall is formed of the porous material, micro-channels are not perfectly separated from each other. Micro-channels may have portions communicated to each other through the pores. A large number of antibody molecules 82 are carried by the pores of honeycomb structure 30. When a mixed sample prepared by mixing the specimen containing antigen molecules 84 as the target and the standard sample is supplied in liquid phase or gas phase to honeycomb structure 30, antigen molecules 84 enter micro-channels 40-50, and further proceed to minute pores 80 of walls 60 forming the inner circumference of micro-channels 40-50. The antigen molecules 84 enter the inside of pores material of honeycomb structure 30 through minute pores 80, though the process of diffusion. Further, antigen molecules 84 encounter antibody molecules 82 carried by minute pores 80 and bonded to antibody molecules 82 by antigen-antibody reaction, generating reactant 88. Most of the generated reactant 88 stays inside the minute pores 80.

Reactant 88 contains antigen derived from the standard sample and antigen derived from the specimen. Antigen derived from the standard sample is labeled with fluorescent dye molecules. Antigen derived from the specimen is not fluorescence-labeled. Honeycomb structure 30 is irradiated with light that excites the fluorescent dye molecules used for fluorescence-labeling and the intensity of generated fluorescence is measured, whereby the amount (concentration) of the antigen in the specimen can be measured, using the calibration curve described above.

Though the antigen-antibody reaction has been described as an example in the present embodiment, the functionalized honeycomb structure in accordance with the present embodiment is also applicable to measurement of target molecule amount in the specimen, utilizing enzyme reaction. When enzyme reaction is used, decomposition of molecules carried in the minute pores of honeycomb structure 30 occurs, or product such as gas molecules result from the reaction. Such reactant can be detected and evaluated mainly by an optical method, using fluorescence excitation characteristic, optical absorption property, chemical luminescence and the like.

<Method of Detecting Reactant>

For the detection of reactant formed by the antigen-antibody reaction described above, a commercially available fluorescence spectrometer, such as Fluorolog manufactured by Jobin Yvon, may be used. Honeycomb structure 30 of the present embodiment, however, also allows detection of the reactant quickly in a simple manner without requiring any expensive device for analysis. In the following the quick and simple method of detecting the reactant will be described.

Figure 6:
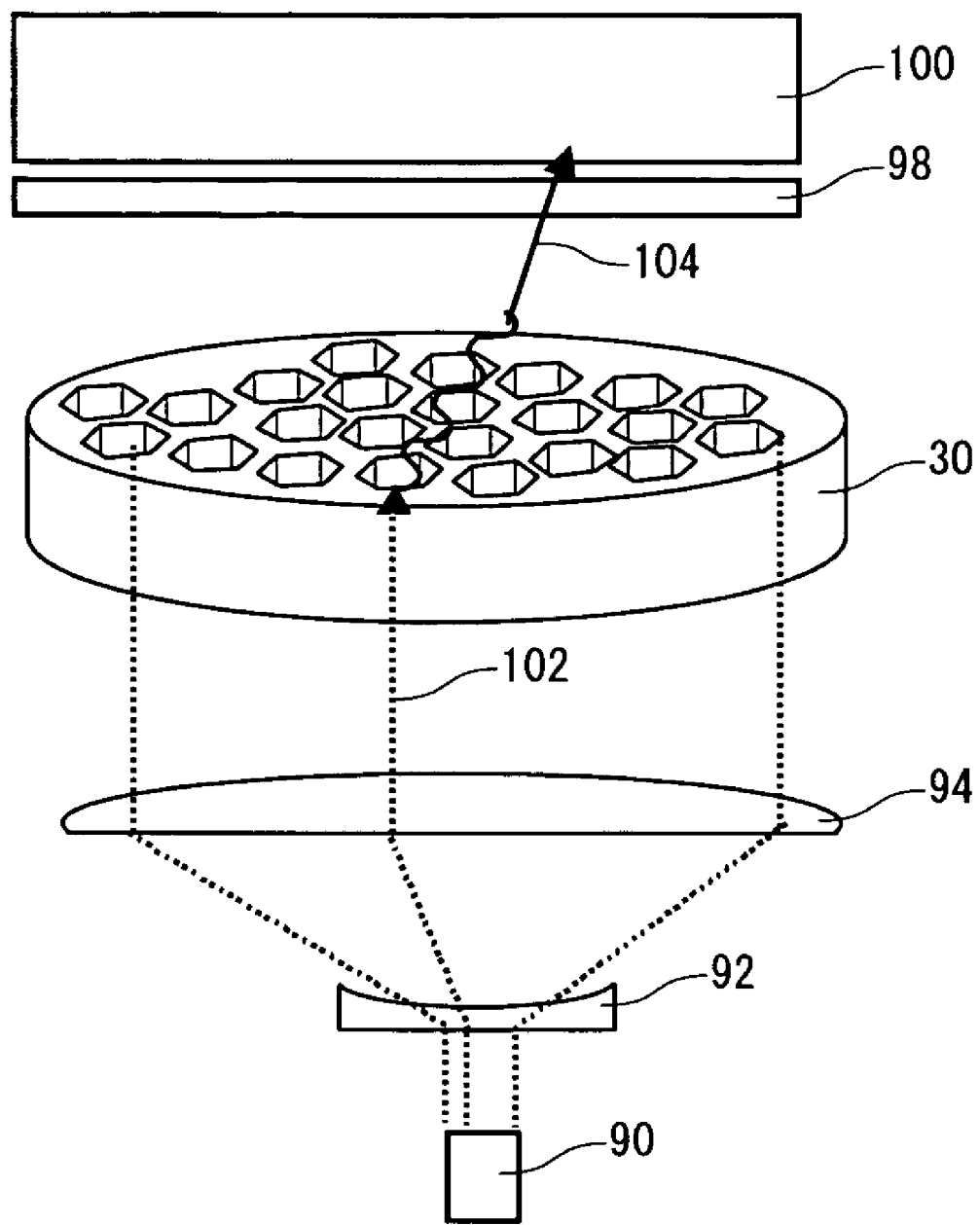
FIG. 6 is an example illustration of a device for optically detecting reactant quickly in a simple manner in accordance with an example embodiment.

FIG. 6 shows a structure of a unit for optically detecting, in a quick and simple manner, the amount of reactant generated by the antigen-antibody reaction, based on fluorescent light from the fluorescent dye molecules for labeling the antigen in the standard specimen. Referring to FIG. 6, the unit includes a semiconductor laser device 90 emitting a laser beam of which wavelength is adjusted to excite the fluorescence-labeled antigen, and a beam expander including a concave lens 92 and a convex lens 94 for converting the laser beam emitted by semiconductor laser device 90 to parallel light beams. The light beams converted by the beam expander will be excitation light 102 of parallel light beams. Excitation light beams 102 are directed to honeycomb structure 30, to be approximately parallel to the axial direction of micro-channels 40. Therefore, the unit shown in FIG. 6 includes a mechanism, not shown, for supporting laser device 90, concave lens 92 and convex lens 94 as well as honeycomb structure 30 such that these components and honeycomb structure 30 are positioned as described above. The fluorescence-labeled antigen in honeycomb structure 30 generates fluorescent light, excited by excitation light beams 102.

The unit further includes an optical filter 98 selectively passing light of a wavelength around the wavelength of excitation light of fluorescence dye molecules used for fluorescence-labeling of the standard sample, and an optical sensor 100 formed of a CCD (Charge Coupled Device) or the like detecting intensity of the light passing through optical filter 98. Optical filter 98 and optical sensor 100 are arranged on one side of honeycomb structure 30 opposite to the side of semiconductor laser 90, to receive fluorescent light 104.

<Operation of Detecting Unit>

Referring to FIG. 6, the detecting unit operates in the following manner. It is assumed that the mixed sample has already been supplied to honeycomb structure 30 and the antigen-antibody reaction has been fully completed. Semiconductor laser device 90 emits a laser beam having a wavelength suitable for exciting the fluorescence-labeled antigen. The laser beam is converted to excitation light beams 102, which are parallel light beams, using the beam expander. Of the reactants of antigen-antibody reaction in honeycomb structure 30, the reactant having the fluorescence-labeled antigen emits fluorescent light 104 as excitation light, when excited by excitation light beams 102. Fluorescent light 104 passes through optical filter 98 and reaches optical sensor 100. Optical sensor 100 measures intensity of fluorescent light 104. Based on the measured intensity of the light, the amount of target (antigen) in the sample is measured, using the calibration curve prepared in advance.

The method of measurement using the unit shown in FIG. 6 can be conducted effectively, utilizing anisotropy of light transmission of honeycomb structure 30. Honeycomb structure 30 has lower transparency in a direction perpendicular to the axis of the micro-channels, as it has periodic structure of porous silica and air in this direction. In the direction parallel to the axis of micro-channels, however, the light passes through the porous silica having uniform transparency, or passes through the air having uniform transparency filled in the micro-channels. Translucency is uniform along the optical path. Therefore, translucency is high in the direction parallel to the axis of micro-channels. Therefore, it is recommendable to adopt the unit structure in which the light is directed in the direction parallel to the axis of micro-channels, and to use laser beam having high parallelism and coherence as a light source. When the laser beam is used, the beam diameter can be enlarged by the beam expander without impairing parallelism of the laser beam. In the structure shown in FIG. 6, in the direction parallel to the axis of micro-channels, translucency is maintained over the optical path length as long as about several hundreds micrometers to several millimeters. As a result, highly sensitive optical measurement becomes possible.

In the embodiment described above, the antigen is used as the target and the antibody is used for the honeycomb structure 30. The present invention, however, is not limited to such an embodiment. Fluorescent light and chemical luminescence may be utilized for detecting reactant resulting from a reaction other than the antigen-antibody reaction. Therefore, the reactant resulting from a reaction other than the antigen-antibody reaction can also be evaluated by the unit structured as described with reference to FIG. 6.

<Method of Fabricating Honeycomb Structure 30>

The method of fabricating the honeycomb structure depends on the substance to be adsorbed and carried. Therefore, specific method of fabrication will be described in detail later with reference to Examples 1 and the others, and only a typical method will be described here. Details of a method of fabricating un-functionalized, simple honeycomb structure is described in S. R. Mukai et al., *Formation of monolithic silica gel microhoneycombs (SMHs) using pseudosteady state growth of microstructural ice crystals*, Chem. Commun., 2004, 874-875.

The honeycomb structure is typically formed in the following manner. Sodium silicate aqueous solution diluted with deionized distilled water is subjected to pH adjustment, and thus, hydrosol is obtained. The hydrosol is put in a container such as a tube formed of polypropylene, and subjected to aging. Thereafter, it is inserted slowly into a cooling bath containing liquid nitrogen or other medium. By this insertion, ice crystal to be a template is formed. Through such steps, the honeycomb structure in accordance with the present embodiment can be fabricated. This method is referred to as unidirectional freeze gelation.

The honeycomb structure fabricated in this manner has a plurality of micro-channels having their axes extending approximately parallel to each other, separated by walls from each other. The substance forming the wall and the inner circumference of the micro-channels has a porous structure having a large number or micro-pores (<2 nm) and meso pores (2 to 50 nm), though it depends on the conditions of formation.

The shape of a micro-channel at a cross-section perpendicular to the channel direction of the micro-channel is generally hexagonal or rectangular, as such shapes are easy to form. The size and diameter of the micro-channel are, dependent of the conditions of fabrication, several micrometers to 200 µm. In the present embodiment, in the process of forming the honeycomb structure, at the state where the silica hydrosol is formed, molecules having the functionality of antibody or the like are mixed. As a result, a functionalized honeycomb structure having molecules applicable to highly sensitive biosensing adsorbed and carried on the walls separating the plurality of micro-channels from each other can be provided.

It is also possible to fabricate a honeycomb structure not carrying the antigen molecules or the like first, and thereafter introducing the molecules having the functionality of antibody or the like to the minute pores of the walls utilizing diffusion process.

Generally, in the method of functionalizing the walls, it is necessary that the functional substance that causes various chemical reactions, chemical bonding or enzyme reaction, including oxidation, reduction and ionization on the chemical substance and biomolecules in the specimen is carried in the minute pores of the walls. For this purpose, the walls must have surface modified or altered or the walls must carry the functional substance. When to introduce the functional substance to be carried on the walls is selected in consideration of the size of biomolecules and the target chemical substance.

By way of example, consider three molecules as stress-related substances, that is, cortisol (MW:362), human CgA (MW:68000) and immunoglobulin A (MW: 200000). Though these are all stress-related substances, they have much different molecular weight. Therefore, corresponding honeycomb bodies are prepared by different methods.

First, cortisol molecule will be considered. Cortisol molecule itself is very small, while anti-cortisol (MW: ~15000) as the antibody to cortisol has the size of about 15 nm. With the size of this level, it is possible to fabricate a porous honeycomb structure carrying anticortisol adsorbed on the silica network, by mixing the substance to hydrogel when the hydrogel is formed by unidirectional freeze gelation. Here, portions of the honeycomb structure not carrying anticortisol have porous structure mainly of meso pores. As the cortisol molecules are small, cortisol diffuses to portions carrying the antibody, and hence, the target can be detected relatively easily.

In contrast, human CgA and immunoglobulin A have larger molecular size, and it is difficult to fabricate the porous honeycomb structure by directly mixing the antibody to hydrogel in the manner as described above. Therefore, for these substances, a honeycomb structure not carrying the antibody is formed first, and thereafter, the size of minute pores is enlarged by processing with ammonia or the like. After the size of minute pores is enlarged, anti-human chromogranin (anti human CgA) and anti-immunoglobulin A are introduced to be adsorbed and carried by the minute pores, utilizing diffusion process from a solution.

<Comparison with Zhou et al.>

Characteristics of the biochemical sensor including honeycomb structure 30 including walls 60 (FIG. 3) separating a plurality of micro-channels 40 (see FIG. 3) in accordance with the present embodiment will be described, in comparison with the porous silica monolith (thickness: 1 mm) in accordance with the disclosure of Zhou et al. and the sol-gel silica thin film (thickness: 1 µm).

Here, again the antigen-antibody reaction will be considered as an example. For comparison, all the materials are set to have outer area of 1 $cm^2$. The amount of carried antibody is in proportion to the volume of each sample, and hence, the amount of antibody carried by each structure (relative value) can be estimated as follows.

| Structure | Size | Amount of carried antibody (relative value) |
|---|---|---|
| Sol-gel silica monolith | 1 cm$^2$ × 1 mm thickness | 1.0 |
| Sol-gel silica thin film | 1 cm$^2$ × 1 μm thickness | 0.001 |
| Honeycomb structure | 1 cm$^2$ × 1 mm thickness | 0.43 |

The antigen as the target encounters the antibody carried by the three different structures, that is, the sol-gel silica monolith, sol-gel silica thin film and the honeycomb structure, and bonded to the antibody by antigen-antibody reaction.

In the sol-gel silica monolith, even when a large amount of antibody is carried, contribution to measurement is small unless the antigen as the target enters the monolith body having the thickness of 1 mm. Assuming that the diffusion time of antigen to the sol-gel silica thin film of 1 μm is about 20 minutes, the diffusion time to the sol-gel silica monolith having the thickness of 1 mm is as long as about 20 min.×10$^6$. This is calculated on the assumption that the diffusion length in the sol-gel silica monolith is in proportion to the root of time. Such a long time for measuring the target is impractical.

For quick measurement, assume that the measurement time is 5 minutes. In that case, the diffusion length of antigen in the monolith body after 5 minutes is 0.5 μm. In the same short diffusion time of 5 minutes, diffusion to the entire thickness of walls is possible in the honeycomb structure in accordance with the present embodiment. The reason for this is that in the honeycomb structure, first, the sample is quickly distributed to the entire honeycomb structure and then enters the minute pores in the walls defining inner circumference of the micro-channels. The wall thickness is comparable to that of silica thin film, in the order of about 0.1 to 10 μm. As can be seen from the experimental results described later, satisfactory result of measurement can be obtained with the wall thickness of about 1 μm and, therefore, thickness of at most 1 μm is particularly desirable. Thus, the antigen spreads over the most part of antibody carried in the minute pores of the walls, causing the antigen-antibody reaction. The antibody carried on the wall surface also contributes to the antigen-antibody reaction, in addition to the antibody held in the minute pores. Thus, the embodiment of honeycomb structure realizes quick and highly sensitive measurement.

The estimated amounts of target introduced to the sample after processing of 5 minutes are as follows.

| Structure | Surface area | Estimated amount of introduced target (relative value) |
|---|---|---|
| Silica monolith | 2 cm$^2$ | 2 × 0.5 = 1 |
| Silica thin film | 1 cm$^2$ | 1 × 0.5 = 0.5 |
| Honeycomb structure | 225 cm$^2$ | 750 × 1 = 750 |

For the estimation, it is assumed here that the micro-channel has an inner diameter of 3 μm and the wall thickness of 1 μm. As can be seen from the foregoing, using the honeycomb structure of the present embodiment, sensitivity can be made two to three orders of magnitude higher than when silica monolith or silica thin film formed of sol-gel method is used.

As described above, the honeycomb structure in accordance with the present embodiment can remarkably increase the surface area that contributes to reaction, as compared with the conventional sol-gel thin film and sol-gel monolith. Further, the antibody is carried on the walls existing between micro-channels. Therefore, as in the case of sol-gel thin film, the target can quickly reach the entire antibody held in the minute pores, realizing quick measurement.

Further, the biochemical sensor using the honeycomb structure in accordance with the present embodiment adopts the honeycomb structure including walls separating a plurality of micro-channels from each other. The wall defining the inner circumference of the micro-channel is formed of a porous material, and capable of carrying a large amount of antibody that reacts to the target, in the minute pores. The specimen sample containing the target is distributed quickly over the walls of the entire honeycomb structure through the micro-channels, and at the entire walls of the honeycomb structure, proceeds to the inside of the walls almost simultaneously. The wall thickness is small and, hence, the target prevails over most of the antibody carried in the walls. Therefore, numerous antigen-antibody reactions take place at one time, allowing quick detection of the target in the sample. As a result, the target detection sensitivity improves and the reaction time can be reduced.

The shape and dimension of the honeycomb structure in accordance with the present embodiment can flexibly be controlled by adjusting the method of fabrication, as will be described later. For quick and highly sensitive measurement, however, it is desired that the micro channel is formed to have the inner diameter of about 1.0 to about 100.0 μm and the wall thickness of about 0.1 to about 10.0 μm.

The biochemical sensor in accordance with the present embodiment has the walls formed by ceramic material such as silica, alumina or titanium oxide. The present invention, however, is not limited to such embodiment, and the honeycomb structure may be fabricated by using a metal base material such as stainless steel or aluminum, coated with such ceramic material. In that case also, the sample enters to the minute pores of the wall from opposite sides thereof, and hence, reaction time can be reduced.

In the embodiment above, for measuring fluorescence intensity, a beam expander is used to attain parallelism of the laser beam from semiconductor laser device 90 (see FIG. 6). The present invention, however, is not limited to such an embodiment. By way of example, the laser beam from the semiconductor laser device may be directed to the sample surface through an optical fiber, and measurement may be done by mechanically moving the optical fiber itself.

Further, in the honeycomb structure and the biochemical sensor using the honeycomb structure in accordance with the present embodiment, the walls separating the plurality of micro-channels are commonly functionalized. By such a structure, a single chemical substance or one type of biomolecules can be detected by the honeycomb structure as a whole. The present invention, however, is not limited to such an embodiment. By way of example, the plurality of walls may be functionalized independently for different targets, or honeycomb structures each functionalized uniquely may be used stacked one after another. By such an arrangement, it becomes possible to detect a plurality of different targets contained in the specimen at one time. When a plurality of honeycomb structures are stacked, the micro-channels of the honeycomb structures may have the same size or different size. By such an arrangement, it becomes possible, for example, to simultaneously measure cortisol, human CgA and immunoglobulin A that are major substances related to mental stress. By this method, not only the data related to one stress-related substance but also a plurality of data can be obtained at one time, and hence, the stress condition can more accurately measured.

The embodiment described above is related to biochemical sensing utilizing the antigen-antibody reaction. The present invention, however, is not limited to such an embodiment, and it is applicable to molecule binding reaction or enzyme reaction, other than the antigen-antibody reaction.

Further, in the present embodiment, a honeycomb structure having a plurality of micro-channels has been described. The structure, however, may have a single micro-channel. Further, though all the micro-channels penetrate from the front surface to the rear surface, some or all of the micro-channels may have bottoms and not penetrate to the rear surface.

Further, the cross-sectional shape of the micro-channel at a plane perpendicularly crossing the axis is hexagonal as an example, and such shape is obtained by self-organization in the process of forming the honeycomb structure. Though micro-channels having hexagonal or rectangular cross section easily form, the shape is not limited to these. It may have other cross-sectional shape, such as triangular shape. Further, the shape may not be a regular shape such as a regular hexagon or square having sides of equal length, but an irregular shape.

Example 1

In the following, a method of fabricating a honeycomb structure adsorbing and carrying anti-cortisol and results of evaluation experiment will be described as Example 1.

By diluting 54% sodium silicate solution with deionized distilled water, 24 mL of sodium silicate aqueous solution having the $SiO_2$ concentration of 1.9 mol/L was obtained. To the sodium silicate aqueous solution, 29 mL of H+ type highly acidic ion exchange resin was added and stirred, and pH of the aqueous solution was adjusted around 3.0 in advance. Thereafter, the ion exchange resin was removed and a few drops of ammonia were added, whereby silica hydrosol having pH of 5.8 was obtained.

To 6 ml of thus obtained silica hydrosol, 9 ml of buffer solution containing 40 µmol of anti-cortisol manufactured by East Coast Biologic (20 mmol phosphate buffer, pH 7.2) was added and mixed. Thereafter, the mixed solution was poured into a tube formed of polypropylene having an inner diameter of 1.0 cm and filled up to 1 cm from the bottom with glass beads, the tube was closed with a lid, and then left stationary at 30° C. Two hours thereafter, the sample that had been left stationary became uniform gel substance.

Two hours after the gelation of the sample, the gel substance was inserted to a coolant bath of ethanol at −20° C. at a constant rate of 2 cm/hour. At this time, because of phase separation of silica hydrogel, ice started to grow in a quasi-steady state from a portion slightly apart from the inserting side end. The growth continued until the entire gel in the polypropylene tube was frozen, and a honeycomb structure was formed with the ice crystal serving as a template.

Thereafter, the sample was put in a constant temperature bath kept at 243K, to stabilize the structure. The eventually obtained sample having the diameter of 1 cm and length of 3 cm was thawed at the room temperature. The sample was taken out from the polypropylene tube and immediately thereafter cut into a thin disk having the thickness of 1.0 mm using a sharp razor.

The resulting sample had a micro-honeycomb structure such as shown in FIG. 3, which had walls 60 having the thickness of about 1 µm, formed to separate a large number of micro-channels 40 having the inner diameter of 3 to 4 µm.

The wall was porous, having meso pores of average pore diameter of 9.2 nm, though the pore size depends on the conditions of formation. The micro-honeycomb structure was dried and then specific surface area thereof was evaluated by BET (Brunauer-Emmett-Teller method). The specific surface area was 80 $m^2$, and meso pore volume was 0.21 $cm^3/g$.

The sample honeycomb structure of thin disk shape obtained in this manner was kept in a phosphate buffer solution until it was used.

[Evaluation Experiment]

Evaluation experiment was conducted on the honeycomb structure adsorbing and carrying anti-cortisol and cut to the thickness of 1 mm formed as described above and on the monolith body formed of the same raw material, for comparing detection sensitivity of target specimen.

The monolith body as an object to be compared was fabricated in the following manner. First, silica hydrosol was mixed with a buffer solution containing anti-cortisol. The mixed solution was poured into a polypropylene container having the inner diameter of 1.0 cm. Then, the container was closed with a lid and left stationary for 2 hours at 30° C. As it was kept stationary, the mixture was gelated, and a monolith body was formed.

The micro-honeycomb structure and the monolith body, kept in the phosphate buffer solution, were taken out immediately before use, to be used for the experiment. The sample for measurement was 300 µl of sample mixture containing 120 µl of 1×PBS, 60 µl of 0.33 mol OG (Oregon Red)—cortisol (cortisol fluorescence labeled with Oregon Red), and 120 µl of serum cortisol standard sample.

In order to observe cortisol concentration dependency, two different serum cortisol standard samples were prepared, that is, samples having cortisol concentration of 10 µl/dl and 100 µl/dl. For fluorescence labeling, fluorescent dye molecules excited by the light having the wavelength of 495 nm and emitting fluorescent light having the wavelength around 527 nm were used.

To quartz containers each filled with 300 µl of sample mixture containing serum cortisol, samples of the honeycomb structure and of the monolith body were immersed, and left for 20 minutes. This was to let the sample for measurement fully penetrate to the entire honeycomb structure and the monolith body. After the samples were taken out from the quartz containers and dried, fluorescence evaluation was performed using the unit having such a structure as shown in FIG. 6.

Referring to FIG. 6, in the present example, a gallium nitride based single quantum well type laser diode having emission wavelength of 495 nm was used as semiconductor laser device 90. The light beam from the laser diode was expanded to excitation light beam 102 as highly coherent parallel light beam having the diameter of 8 mm using a beam expander including lenses 92 and 94, and directed to honeycomb structure 30 (and monolith body). Fluorescent light 104 generated by honeycomb structure 30 (and monolith body) by laser beam excitation passes through a band pass filter 98 adapted to selectively pass the light of prescribed fluorescence wavelength (around 527 nm). As a result, only the light of prescribed fluorescence wavelength is selectively obtained, from the fluorescent light 104. Thereafter, using a silicon CCD 100, spectral intensity of the light that has passed through optical filter 98 having the wavelength around 527 nm was measured. In the measurement, each pixel of the CCD receives the same fluorescent light. Therefore, by accumulation of the pixel signals, highly sensitive measurement is possible.

Figure 7:
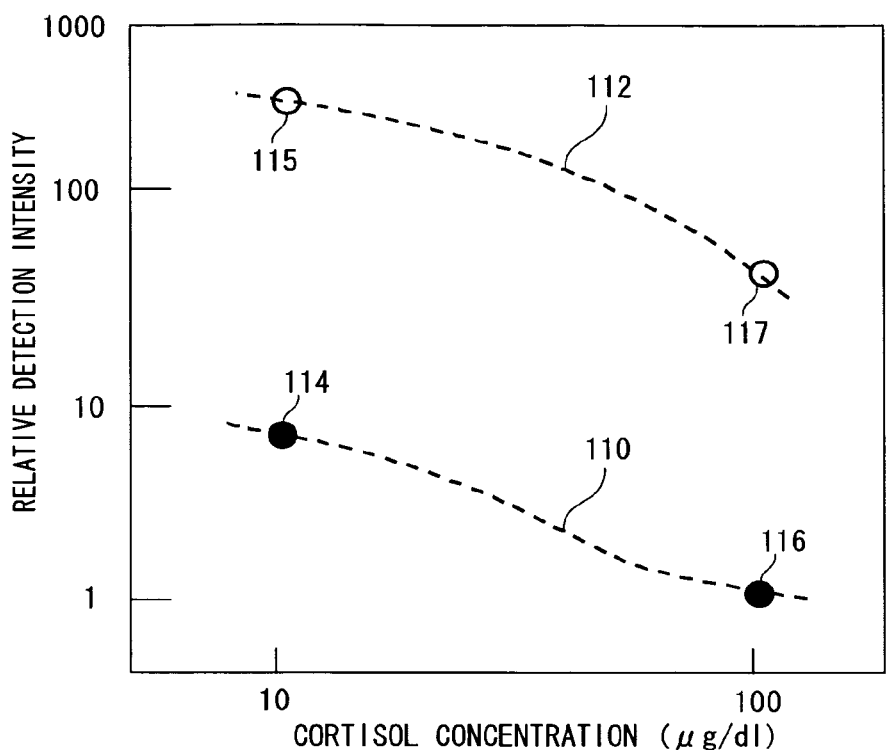
FIG. 7 is a graph representing result of example evaluation Experiment 1.

FIG. 7 is a graph plotting the detected fluorescent light intensity as the accumulated value from the micro-honeycomb structure and the monolith body with respect to the amount of cortisol in the serum standard sample. Referring to FIG. 7, a curve 110 represents the result when the monolith body was used. A curve 112 represents the result when the honeycomb structure was used. In the measurement, the phenomenon was utilized that, because of competing assay, the fluorescent light derived from OG-cortisol is weakened by the serum cortisol as the target sample. Namely, when the amount of cortisol in the specimen increases relative to the serum cortisol, relative detection intensity decreases.

As can be seen from FIG. 7, with the cortisol amount of 10 µl/dl (114 and 115) and 100 µl/dl (116 and 117), the detected fluorescent light intensity of the honeycomb structure was one to two orders of magnitude higher than that of the monolith body. Therefore, it can be understood that the target detection sensitivity of the micro-honeycomb structure of the present example was far higher than the target detection sensitivity of the monolith body.

Example 2

In the following, a method of fabricating a honeycomb structure adsorbing and carrying anti-human CgA and results of evaluation experiment will be described as Example 2. In the present example, the target is human CgA, and fluorescence intensity analysis is done based on the reactant produced by the anti-human CgA-human CgA reaction between human CgA and anti-human CgA.

In the present example, the honeycomb structure was fabricated in the following manner. First, by diluting 54% sodium silicate solution with deionized distilled water, 24 mL of sodium silicate aqueous solution having the $SiO_2$ concentration of 1.9 mol/L was obtained. To the sodium silicate aqueous solution, 29 mL of H+ type highly acidic ion exchange resin was added and stirred, and pH of the aqueous solution was adjusted around 2.5 and thus silica hydrosol was obtained. Thereafter, 6 ml of thus obtained silica hydrosol was poured into a tube formed of polypropylene having an inner diameter of 1.0 cm and filled up to 1 cm from the bottom with glass beads, the tube was closed with a lid, and then left stationary at 30° C. Two hours thereafter, the sample that had been left stationary became uniform gel substance.

Two hours after the gelation of the sample, the gel substance was inserted to a coolant bath of ethanol at −30° C. at a constant rate of 2 cm/hour. At this time, because of phase separation of silica hydrogel, ice started to grow in a quasi-steady state from a portion slightly apart from the inserting side end. The growth continued until the entire gel in the polypropylene tube was frozen.

Thereafter, the sample was put in a constant temperature bath kept at 243K, and kept at the constant temperature for 2 hours. By this process, strength of the micro-honeycomb structure having the ice crystal serving as the template was reinforced. The sample obtained in this manner was thawed at the room temperature and taken out from the tube. The sample was immersed in 12% ammonia water at 25° C. for 24 hours, to enlarge the size of minute pores.

The sample was immersed in t-butanol, and with sufficient time, ammonia water as the solvent was replaced by t-butanol. Here, the sample was again freeze-dried at −10° C., and the honeycomb structure shape was obtained. The obtained sample was cut into thin disk having the thickness of 1 mm using a sharp razor. The sample was annealed for 30 minutes at 900° C. in a furnace whose inside air was replaced by pure nitrogen. This was to improve structural strength and translucency of the sample.

The obtained sample was immersed in a solution containing 0.27 µmol of anti-human CgA (manufactured by Yanaihara Institute Inc.) and 12 ml of distilled water for 24 hours, and thus, a honeycomb structure adsorbing and carrying anti-human CgA was obtained.

The sample obtained in this manner had a micro-honeycomb structure such as shown in the cross-sectional view of FIG. 3, which had walls 60 having the thickness of about 1 µm, formed to separate a large number of micro-channels 40 having the inner diameter of 3 to 4 µm. Walls 60 had mesoporous structure.

The micro-honeycomb structure was evaluated by BET method, and from the result, the average pore diameter was 18.6 nm, surface area was 13.0 $m^2$/g, and meso pore volume was 0.36 $cm^3$/g.

[Evaluation Experiment]

Using the honeycomb structure adsorbing and carrying the anti-human CgA and cut to the thickness of 1 mm fabricated in the above-described manner, measurement was done, with salivary human CgA being the target. The measurement was done in accordance with a protocol "YK070 Human Chromogranin A EIA" by Yanaihara Institute Inc.

Specifically, saliva sample of 800 µl was put in a saliva sampling tube manufacture by Starsted, Germany, which was subjected to centrifugal separation of 3000 rpm. Then, the saliva sample was put in a small tube of polypropylene, and kept at −30° C. The saliva sample was used as the specimen.

Standard liquid samples, each of 200 µl, having standard human CgA antigen (Yanaihara Institute Inc.) dissolved and diluted in phosphate buffer solutions to the concentration of 30 pmol, 10 pmol, 1 pmol and 0.3 pmol were prepared. Then, five quartz containers having the size of 1.2 cm×1.2 cm and the depth of 5 mm were prepared. To each of the containers, 400 µl of sample mixture containing 100 µl of 1×PBS, 100 µl of biotin labeled human CgA antigen solution and 200 µl of standard human CgA antigen, or 400 µl of sample mixture containing 100 µl of 1×PBS, 100 µl of biotin labeled human CgA antigen solution and 200 µl of saliva sample specimen was poured and stirred. Thereafter, the honeycomb structure adsorbing and carrying the anti-human CgA fabricated in the above-described manner was immersed in the sample mixture. Then, the honeycomb structure carrying the anti-human CgA was left for 8 hours, so that the honeycomb structure was fully impregnated with the measurement sample.

The mixture in each quartz container was removed, and the quartz containers were washed. Then, 200 µl of HRP (Horseradish Peroxidase) bonded Streptavidin solution was put in each quartz container and reaction was caused, for two hours.

Thereafter, the solution was removed from each of the quartz containers, and the quartz containers were washed. Then, 100 µl of solution prepared by dissolving a tablet of O-phenylene diamine in 25 ml of 0.1 mol phosphate-citric acid buffer solution containing 0.15% hydrogen peroxide was poured to each quartz container. The mixed solution and the honeycomb structure were kept at the room temperature to cause reaction for 30 minutes, and then, the containers were washed again. Then, five honeycomb structures processed in this manner were taken out from the quartz containers and set in an absorptiometer.

Figure 8:
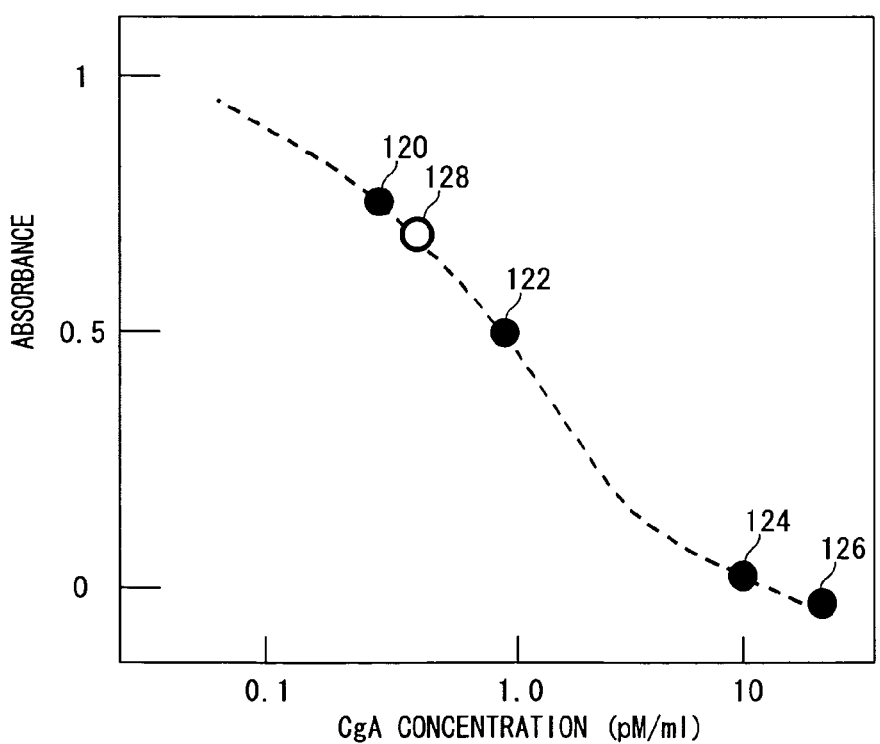
FIG. 8 is a graph representing result of example evaluation Experiment 2.

FIG. 8 is a graph representing the result of evaluation experiments. The ordinate represents absorbance, and the abscissa represents concentration of human CgA. Black circles 120, 122, 124 and 126 represent human CgA standard samples, and a white circle 128 represents the saliva specimen.

Referring to FIG. 8, measurement data 120, 122, 124 and 126 of human CgA standard samples represented by black circles and measurement data 128 of saliva specimen represented by a white circle were compared. Detection of standard sample having the concentration as low as 0.3 pmol/ml was possible. The human CgA concentration (white circle 128) of the saliva specimen measured was 0.43 pmol/ml. It can be understood that the method of measurement in accordance with Example 2 allows satisfactory measurement of human CgA concentration of saliva specimen.

Example 3

Figure 9:
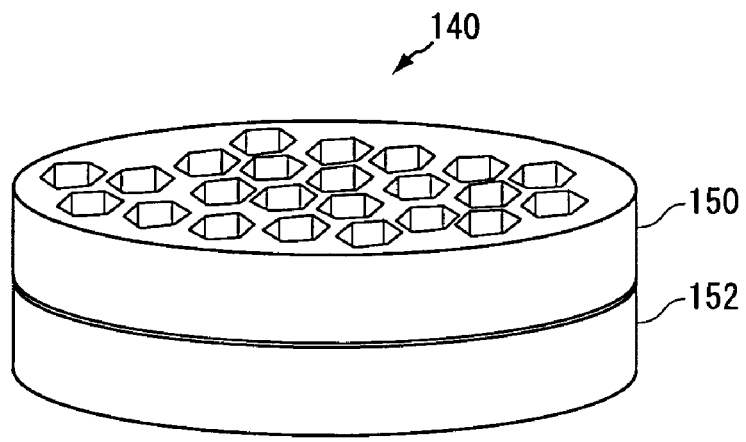
FIG. 9 is a perspective view showing an example embodiment of honeycomb structure having a two-layered stacked structure of Experiment 3.

As Example 3, a two-layered structure such as shown in FIG. 9 was formed by stacking disk-shaped honeycomb structures fabricated in accordance with Examples 1 and 2. The result of evaluation experiment on the stacked honeycomb structure will be described in the following. The stacked honeycomb structure of the present example can readily be formed by stacking the micro-honeycomb structures described with reference to Examples 1 and 2. Therefore, description of the fabricating method will not be repeated.

[Evaluation Experiment]

FIG. 9 shows a two-layered, stacked disk-shaped honeycomb structure 140. Referring to FIG. 9, the two-layered, disk-shaped honeycomb structure 140 includes a honeycomb structure 152 having the same structure as the honeycomb structure fabricated in accordance with Example 2, and a honeycomb structure 150 having the same structure as the honeycomb structure fabricated in accordance with Example 1, having channels same in shape as the channels of honeycomb structure 152 and stacked on honeycomb structure 152 such that the channels are positioned continuous to the channels of honeycomb structure 152.

Using the two-layered, disk-shaped honeycomb structure 140, the inventors simultaneously measured cortisol and human CgA in saliva specimen. The saliva sample used was the same as that used in Example 2.

A quartz container having the size of 1.2 cm×1.2 cm and the depth of 5 mm was prepared. To the container, 400 µl of sample mixture containing 50 µl of 1×PBS, 100 µl of biotin-labeled human CgA antigen solution, 50 µl of 0.33 mol OG-corsitol and 200 µl of saliva sample specimen was poured and stirred. The stacked type honeycomb described above was immersed in the mixed solution, and left for 24 hours, so that the micro-honeycomb structure was fully impregnated with the measurement sample.

Thereafter, the liquid in the quartz container was removed, the container was washed, and then, 400 µl of Streptavidin solution fluorescent-labeled with Texas Red was poured to the quartz container. Reaction between the solution and the sample was continued for 2 hours. Thereafter, the sample was further washed and dried. After the end of processing, the two-layered stacked honeycomb was taken out from the quartz container, and fluorescence measurement was conducted.

In the fluorescence measurement, a gallium nitride based single quantum well type laser diode having emission wavelength of 495 nm was used for fluorescent excitation. Fluorescent light having the wavelength of 527 nm of Oregon Green, derived from cortisol, and fluorescent light having the wavelength of 615 nm of Texas Red derived from human CgA were detected. As a result, it was confirmed that the two stress-related substances could be evaluated at one time.

Further, as to the amount of stress-related substances measured by the present method, cortisol was 8.4 pmol/ml and human CgA was 0.21 pmol/ml.

Example 4

In the following, a method of fabricating a honeycomb structure adsorbing and carrying horse myoglobin and the result of evaluation experiment thereof will be described.

In the present example, horse myoglobin-carbon monoxide reaction is utilized. The minute pores of the walls of honeycomb structure adsorb and carry horse myoglobin, and carbon monoxide as the target is supplied to the honeycomb structure. As a result, by the horse myoglobin-carbon monoxide reaction between the horse myoglobin adsorbed and carried by the honeycomb structure and carbon monoxide, a reactant is generated. By measuring the fluorescence intensity of the reactant, concentration of carbon monoxide is measured.

By diluting 54% sodium silicate solution with deionized distilled water, 24 mL of sodium silicate aqueous solution having the $SiO_2$ concentration of 1.9 mol/L was obtained. To the sodium silicate aqueous solution, 29 mL of H+ type highly acidic ion exchange resin was added and stirred, and pH of the aqueous solution was adjusted around 3.0 in advance. Thereafter, the ion exchange resin was removed and a few drops of ammonia was added, whereby silica hydrosol having pH of 5.8 was obtained.

Thereafter, to the thus obtained silica hydrosol, 9 ml of myoglobin solution having 2 mM of horse myoglobin of Sigma Chemical added, was added and mixed. Thereafter, the mixed solution was poured into a tube formed of polypropylene having an inner diameter of 1.0 cm and filled up to 1 cm from the bottom with glass beads, the tube was closed with a lid, and then left stationary at 30° C. Two hours thereafter, the sample that had been left stationary became uniform gel substance.

Two hours after the gelation of the sample, the gel substance was inserted to a coolant bath of ethanol at −20° C. at a constant rate of 2 cm/hour. At this time, because of phase separation of silica hydrogel, ice started to grow in a quasi-steady state from a portion slightly apart from the inserting side end. The growth continued until the entire gel in the polypropylene tube was frozen, and a honeycomb structure was formed with the ice crystal serving as a template.

Thereafter, the sample was put in a constant temperature bath kept at 243K, and kept for 2 hours. The eventually obtained sample having the diameter of 1 cm and length of 3 cm was thawed at the room temperature. The sample was taken out from the polypropylene tube and immediately thereafter cut into a thin disk having the thickness of 1.0 mm using a sharp razor.

The resulting sample had a micro-honeycomb structure such as shown in FIG. 3, which had walls 60 having the thickness of about 1 µm, formed to separate a large number of micro-channels 40 having the inner diameter of 3 to 4 µm. The wall was porous, having meso pores of 2 to 50 nm in pore diameter, though the pore size depends on the conditions of formation. The micro-honeycomb structure was dried and then specific surface area thereof was evaluated by BET. The specific surface area was 90 $m^2$, and meso pore volume was 0.17 $cm^3/g$.

The sample honeycomb structure of thin disk shape obtained in this manner was kept in a phosphate buffer solution until it was used.

[Evaluation Experiment]

Evaluation experiment was conducted on the honeycomb structure adsorbing and carrying horse myoglobin fabricated in the above-described manner, for evaluating detection sensitivity of detecting carbon monoxide.

The honeycomb structure adsorbing and carrying horse myoglobin was set in a container of 10 cm×10 cm, and exposed to air containing 1000 ppm of carbon monoxide.

As a result, at the wavelength of 470 nm that corresponds to generation of carboxyl myoglobin from oxymyoglobin, absorption coefficient decreased. This means that carbon monoxide was bonded to horse myoglobin adsorbed and carried by the honeycomb structure.

Example 5

In the following, a method of manufacturing a honeycomb structure adsorbing and carrying HRP and GOD (glucose oxidase) and the result of evaluation experiment will be described as Example 5.

By diluting 54% sodium silicate solution with deionized distilled water, 24 mL of sodium silicate aqueous solution having the $SiO_2$ concentration of 1.9 mol/L was obtained. To the sodium silicate aqueous solution, 29 mL of $H^+$ type highly acidic ion exchange resin was added and stirred, and pH of the aqueous solution was adjusted around 3.0 in advance. Thereafter, the ion exchange resin was removed and a few drops of ammonia was added, whereby silica hydrosol having pH of 5.8 was obtained.

Meanwhile, 10 mg of HRP and 25 ml of GOD of 5000 U were added to phosphate buffer solution of pH 6.0, and a HRP/GOD solution was prepared. Thereafter, 10 ml of the HRP/GOD solution was mixed in 10 ml of the silica sol. Thereafter, the mixed solution was poured into a tube formed of polypropylene having an inner diameter of 1.0 cm and filled up to 1 cm from the bottom with glass beads, the tube was closed with a lid, and then left stationary at 30° C. Two hours thereafter, the sample that had been left stationary became uniform gel substance.

Two hours after the gelation of the sample, the gel substance was inserted to a coolant bath of ethanol at −20° C. at a constant rate of 2 cm/hour. At this time, because of phase separation of silica hydrogel, ice started to grow in a quasi-steady state from a portion slightly apart from the inserting side end. The growth continued until the entire gel in the polypropylene tube was frozen, and a honeycomb structure was formed with the ice crystal serving as a template.

Thereafter, the sample was put in a constant temperature bath kept at 243K, and kept for 2 hours. The eventually obtained sample having the diameter of 1 cm and length of 3 cm was thawed at the room temperature. The sample was taken out from the polypropylene tube and immediately thereafter cut into a thin disk having the thickness of 1.0 mm using a sharp razor.

The resulting sample had a micro-honeycomb structure such as shown in FIG. 3, which had walls 60 having the thickness of about 1 μm, formed to separate a large number of micro-channels having the inner diameter of 3 to 4 μm. The wall was porous, having meso pores of 2 to 50 nm in pore diameter, though the pore size depends on the conditions of formation. The porous structure was dried and then specific surface area thereof was evaluated by BET. The specific surface area was 60 m$^2$, and meso pore volume were 0.48 cm$^3$/g and 0.11 cm$^3$/g, respectively.

The sample honeycomb structure of thin disk shape obtained in this manner was kept in a phosphate buffer solution until it was used.

[Evaluation Experiment]

Glucose detection test was conducted on the honeycomb structure adsorbing and carrying HRP/GOD and cut to the thickness of 1 mm, fabricated as Example 5. A standard sample of glucose was prepared in the following manner. Specifically, glucose was diluted using Ringer's solution containing 148 mM of NaCl, 4.0 mM of KCl and 2.3 mM of CaCl2. Thus, standard samples having the concentration of 0.8 to 10 mM/l were prepared.

As a reagent for detecting $H_2O_2$ generated by the reaction between the enzyme and glucose with high sensitivity, luminol solution was prepared by adding 1.8 g of luminol and 4 g of NaCl to diluted water of 1000 ml.

In quartz containers each filled with 150 ml of standard samples of different glucose concentration, the sample honeycomb structures were immersed and left for 3 hours, so that the honeycomb structures were fully impregnated with the measurement samples.

The quartz containers were washed with distilled water, and the distilled water in the containers was replaced by the luminol solution described above, and the samples were put and kept therein for 10 minutes. The honeycomb structures were then taken out from the quartz containers and dried, and fluorescence evaluation of the samples was conducted in a manner as shown in FIG. 6.

Referring to FIG. 6, first, light was emitted from a gallium nitride based single quantum well type laser diode 90 having emission wavelength of 495 nm as the semiconductor laser device. The emitted light was expanded by a beam expander formed of lenses 92 and 94 to excitation light 102 as highly coherent parallel light beams, and directed to the sample honeycomb structures. Fluorescent light 104 emitted from the samples because of laser beam excitation was filtered through optical filter 98, and of the resulting light, spectral intensity of light having fluorescent wavelength around 590 nm only was measured by using a CCD 100. In the present example, highly sensitive measurement was made by accumulating pixel signals output from the CCD.

Figure 10:
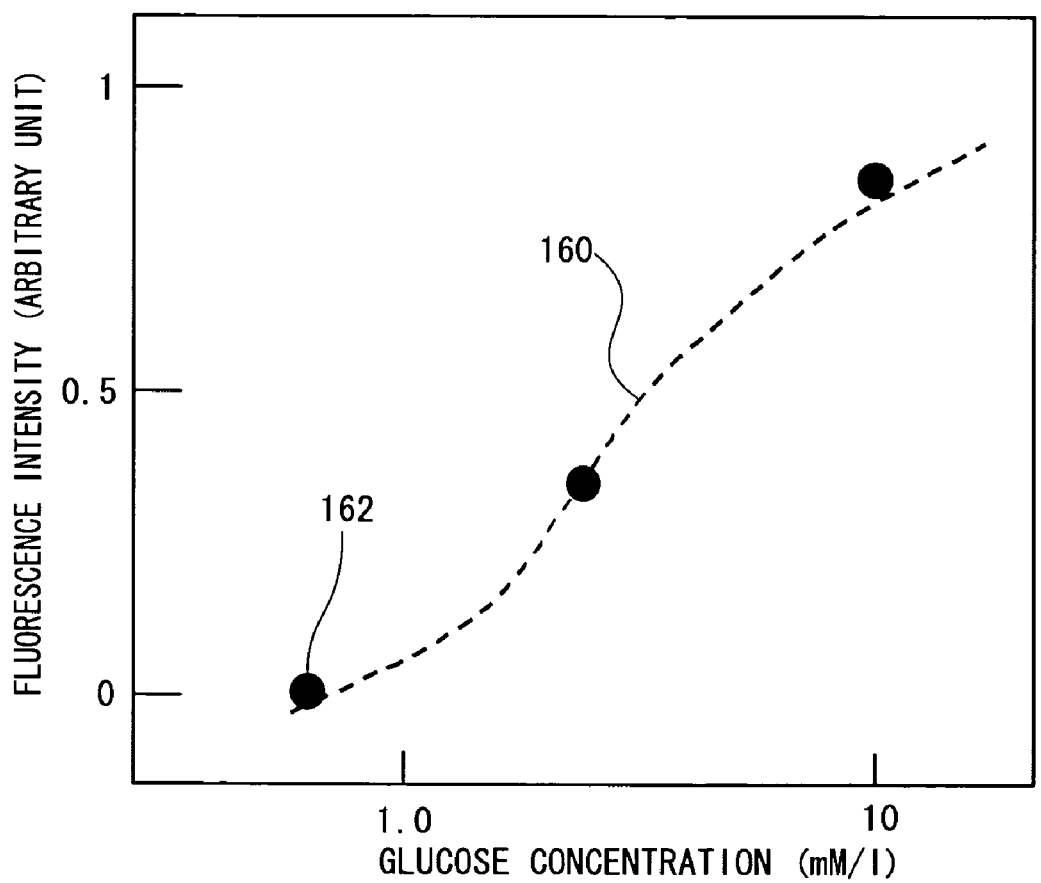
FIG. 10 is a graph representing result of example evaluation Experiment 3.

By plotting the detected fluorescence intensity obtained as the accumulated value from the glucose standard samples against the glucose concentration of respective samples, a graph is formed. FIG. 10 is the graph, in which the ordinate represents fluorescence intensity, and the abscissa represents glucose concentration. A curve 160 represents the relation between the glucose concentration and the fluorescence intensity. As can be seen from FIG. 10, collected data indicated that as the glucose concentration increased, detected fluorescence intensity increased. Further, measurement with sufficient sensitivity could be made even with the lowest glucose concentration of 0.8 mM/l (162).

In the embodiment described above, the channels had regular hexagonal cross-sections. The present invention, however, is not limited to such an embodiment, and the channels may have any polygonal shape other than the hexagon, and it need not be a regular polygon. Further, it is unnecessary that all channels have the same cross-sectional shape. Actually, however, it is preferred to utilize self organization observed in the nature to form the minute channels, and hence, the shape would be defined by the self organization. As a result, it is often the case that channels having regular polygonal cross section and of the same size and direction are arranged to form a two-dimensional matrix with the same space on the left, right, top and bottom of each channel, both on the upper and lower surfaces, as in the embodiment described above.

There may be only one channel, or a plurality of channels. Though the central axes of channels were parallel to each other in the embodiment described above, they may not necessarily be parallel to each other. Here again, when self organization observed in the nature is utilized for forming the sensor, it would be often the case that a plurality of mutually parallel channels are formed.

The embodiments as have been described here are mere examples and should not be interpreted as restrictive. The scope of the present invention is determined by each of the claims with appropriate consideration of the written description of the embodiments and embraces modifications within the meaning of, and equivalent to, the languages in the claims.

What is claimed is:

1. A biochemical sensor for detecting a prescribed target substance contained in a specimen of liquid phase or gas phase, including:
   a first layer sensor, and
   a second layer sensor arranged on said first layer sensor,
   each of said first layer sensor and said second layer sensor including:
      a sensor structure wherein a channel is formed to penetrate from a first surface to a second surface of the structure, allowing influx of said specimen, an inner circumferential surface of said channel being comprised of a porous material; and
      a functional substance carried in said porous material forming the inner circumferential surface of said channel, the functional substance configured to form reactant by interaction with said prescribed target substance;
   wherein the functional substance carried by said first layer sensor is different from the functional substance carried by said second layer sensor,
   wherein a cross section of said channel is hexagonal; and,
      wherein the first layer comprises plural channels and the second layer comprises plural channels, and wherein the channels of the first layer sensor and the channels of the second layer sensor have different sizes.

2. The biochemical sensor according to claim 1, wherein said prescribed target substance includes a prescribed antigen; and
said functional substance includes an antibody causing an antigen-antibody reaction with said prescribed antigen.

3. The biochemical sensor according to claim 1, wherein said prescribed functional substance is an enzyme; and
said prescribed target substance generates a known reactant by a prescribed reaction caused in the presence of said enzyme.

4. The biochemical sensor according to claim 1, wherein said sensor structure is formed of a ceramic material; and
the inner circumferential surface of said channel is formed of said ceramic material of said sensor structure.

5. The biochemical sensor according to claim 1, wherein said sensor structure is formed of a prescribed metal base formed in a shape having a through hole, and a prescribed ceramic material coated on a surface of said metal base; and
the inner circumferential surface of said channel is defined by a surface of said ceramic material coated on the inner circumferential surface of said through hole of said sensor structure.

6. The biochemical sensor according to claim 1, wherein said sensor structure is formed of a prescribed translucent porous material; and
the inner circumferential surface of said channel is formed of said porous material of said sensor structure.

7. The biochemical sensor according to claim 1, wherein said sensor structure has a cylindrical shape having a first end surface, a second end surface parallel to said first end surface, and a side surface connecting outer circumferences of said first end surface and said second end surface; and
each of said plurality of channels is formed to connect said first end surface to said second end surface.

8. The biochemical sensor according to claim 7, wherein each of said plurality of channels is formed with central axis of each of the channels being parallel to each other.

9. The biochemical sensor according to claim 8, wherein each of said plurality of channels has a same shape at a cross section in a prescribed direction crossing said central axis.

10. The biochemical sensor according to claim 7, wherein said plurality of channels are arranged such that openings of said plurality of channels form, on said first surface, a two-dimensional matrix spaced with the same space on the left, right, top and bottom, from each other.

11. The biochemical sensor according to claim 7, wherein said first end surface and said side surface are perpendicular to each other.

12. The biochemical sensor according to claim 7, wherein said plurality of channels are separated by a wall from each other, and thickness of the wall on a line connecting central axes of adjacent channels is at most 1 μm.

13. The biochemical sensor according to claim 1, wherein said sides of the hexagonal channel are equal in length with each other.

14. The biochemical sensor according to claim 1, wherein the functional substance carried by said first layer sensor is the same as the functional substance carried by said second layer sensor.

15. The biochemical sensor according to claim 1, wherein sensor structures of said first layer sensor and said second layer sensor are formed such that said channels have mutually matching shape, size and arrangement, and said first layer sensor and said second layer sensor are arranged such that mutual channel positions match with each other.

16. A biochemical sensor according to claim 1 wherein the functional substance carried by the first layer sensor and the functional substance carried by the second layer sensor are chosen to detect a plurality of different prescribed target substances at a same time.

* * * * *